United States Patent [19]
Filis

[11] Patent Number: 6,004,342
[45] Date of Patent: Dec. 21, 1999

[54] NASAL INSERT DEVICE FOR IMPROVING BREATHING

[76] Inventor: Elias A. Filis, 495 King Arthur Dr., Franklin, Ind. 46131

[21] Appl. No.: 09/048,354

[22] Filed: Mar. 26, 1998

[51] Int. Cl.[6] .................................................. A61M 29/00
[52] U.S. Cl. ............................................................ 606/199
[58] Field of Search .................................. 606/199, 162, 606/161, 204.35

[56] References Cited

U.S. PATENT DOCUMENTS

| | | | |
|---|---|---|---|
| 1,597,331 | 8/1926 | Thurston . | |
| 2,335,936 | 12/1943 | Hanlon | 128/342 |
| 2,672,138 | 3/1954 | Carlock | 606/199 |
| 3,424,152 | 1/1969 | Kuhlman | 128/132 |
| 3,710,799 | 1/1973 | Caballero | 128/342 |
| 4,105,035 | 8/1978 | Rella | 128/342 |
| 4,120,299 | 10/1978 | Russo | 128/140 |
| 4,414,977 | 11/1983 | Rezakhany | 128/342 |
| 5,067,482 | 11/1991 | Reid | 606/204.35 |
| 5,533,503 | 7/1996 | Doubek et al. | 128/200.24 |
| 5,549,103 | 8/1996 | Johnson | 128/200.24 |
| 5,553,605 | 9/1996 | Muchin | 128/200.24 |
| 5,611,355 | 3/1997 | Hilsen | 128/848 |
| 5,653,224 | 8/1997 | Johnson | 128/200.24 |
| 5,665,104 | 9/1997 | Lee | 606/199 |

*Primary Examiner*—Michael Buiz
*Assistant Examiner*—Jackie Tan-Uyent T. Ho
*Attorney, Agent, or Firm*—Woodard, Emhardt, Naughton Moriarty & McNett

[57] ABSTRACT

A nasal passage device comprising a pair of hollow nasal inserts shaped to conform to the wearer's nasal passages and worn inside the nose and having a handle portion which connects the pair of nasal inserts.

19 Claims, 2 Drawing Sheets

NASAL INSERT DEVICE FOR IMPROVING BREATHING

TECHNICAL FIELD OF THE INVENTION

The present invention relates generally to the field of devices for improving breathing. The present invention relates more specifically to the use of a nasal insert that improves breathing.

BACKGROUND OF THE INVENTION

Many people are afflicted with some degree of snoring. Snoring is not only an annoyance to others, but may be symptomatic of an underlying breathing problem. Snoring happens when turbulent air causes the uvula, soft palate, and base of the tongue to vibrate against the posterior wall of the pharynx, producing the rough snoring noise. Snoring noise levels can range from the barely audible to almost 90 dB. Snoring can cause the snorer humiliation, embarrassment, and emotional distress in addition to the daytime sleepiness, listlessness, and reduced disease resistance caused by lack of restful sleep in both the snorer and those around him.

Snoring can occur as a result of partially blocked or obstructed nasal passages, such as an occlusion of the pharynx over an area extending from the base of the tongue inferiorly to the uvula and soft palate superiorly. The obstructions can either directly increase the turbulence of the air flowing from the nasal passages or urge breathing through the mouth. Both situations can result in vibration of the uvula, soft palate, and tongue against the pharynx wall to produce snoring.

In the former case, air is drawn through the nostrils into the nasal cavities. The air proceeds through the tapering cavities, through a narrow nasal valve, and then through a widening passageway that ultimately leads from the nose to the lungs. Most obstructions occur at or near the nasal valve where the air flow is most constricted. The tissue comprising the walls of the nasal cavity can become so loose that during inhalation the walls are drawn in and collapse into the nasal valve, partially or completely blocking it. When this happens during sleep, snoring can result. A more serious result of nasal passage obstruction is that the sleeper may get insufficient oxygen. In the extreme case this condition is known as sleep apnea. People suffering from sleep apnea do not receive the full restful benefits from sleep and tend to be tired throughout the day.

In the latter case of preferential mouth breathing, throat and lung irritation may result from the inhalation of air that has not undergone warming and/or filtration through the nose. Such physical irritation may lead to sore throats, coughs, or increases incidence of infection due to the presence of foreign particles that would otherwise be filtered by the nose, in addition to sleep disturbances.

A further problem that may be experienced is the inability to breath through the nose during eating. Such a problem may result in both physical (choking) and social consequences.

Perhaps the most common prescribed treatments of serious and chronic nasal obstruction are corrective surgery and adherence to a strict and demanding medical regimen. However, these options are not acceptable to all patients, and may not be appropriate for those with more minor afflictions. In addition to being expensive, these treatments are often only partially successful and the problem may recur and worsen over time.

Devices known as nasal dilators have been developed as alternatives to surgery. One class of dilators are those worn on the exterior of the nose. These dilators attach to the outside of the nose and exert a tensile force on the nose to pull the nasal passages open. Examples of these in the prior art include U.S. Pat. No. 5,653,224 to Johnson, U.S. Pat. No. 5,553,605 to Muchin, U.S. Pat. No. 5,533,503 to Doubek et al., and U.S. Pat. No. 5,549,103 to Johnson. While useful, these external dilators have the drawbacks of being unsightly and uncomfortable. They are also limited to addressing obstructions located under the skin that the dilators attach to on either side of the nose. Finally, the amount of tensile force the external dilator may apply must be less than the adhesive force used to attach it to the exterior of the nose.

Examples of internally worn nasal dilators in the prior art include U.S. Pat. No. 5,665,104 to Lee, U.S. Pat. No. 4,414,977 to Rezakhany, U.S. Pat. No. 4,120,299 to Russo, U.S. Pat. No. 4,105,035 to Rella, U.S. Pat. No. 3,710,799 to Caballero, U.S. Pat. No. 3,424,152 to Kuhlman, U.S. Pat. No. 2,672,138 to Carlock, U.S. Pat. No. 2,335,936 to Hanlon, and U.S. Pat. No. 1,597,331 to Thurston et al. These include nasal inserts of various designs, such as cages, frameworks, tubes, and balls to be inserted into the nasal passages.

Hence, there is a need for an improved nasal cavity insert.

SUMMARY OF THE INVENTION

The present invention relates generally to an improved device for improving air flow through the nasal passages. The present invention has one form wherein a semi-rigid elastomeric material is molded into a pair of connected hollow tubes with exterior shapes conforming to at least a portion of the nasal cavities of the wearer. The present invention has another form wherein the semi-rigid material is a dental elastomer, such as vinyl poly siloxane or the like. The material used for the insert is contemplated to be any material known to those of ordinary skill in the art that has similar rigidity, flexibility and nasal comfortability as the above mentioned materials.

One form of the present invention contemplates a semi-rigid hollow nasal insert to be worn inside the nasal cavities.

One object of the present invention is to provide a means for improving air flow through the nasal passages.

Another object of the present invention is to prevent and/or reduce snoring by improving the air flow through the nasal passages during sleep.

Still another object of the present invention is to provide a means for comfortably keeping the nasal passages from collapsing while breathing.

Related objects and advantages of the present invention will be apparent from the following description.

DETAILED DESCRIPTION OF THE PREFERRED EMBODIMENT

Figure 1:
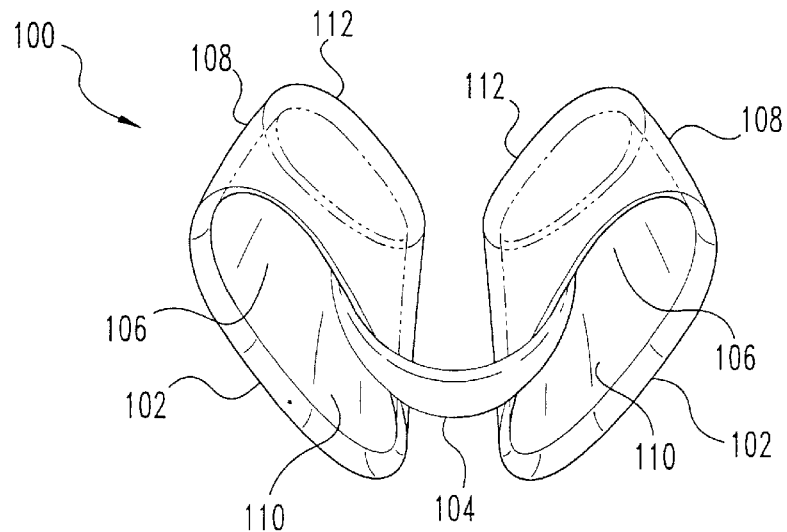
FIG. 1 is an isometric view of a preferred embodiment of the invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, a first embodiment nasal device 100 is shown having a pair of nasal inserts 102 joined by a connecting strip 104. Preferably, the outer surface 108 of each insert 102 is molded to the shape of the nasal passage (see FIG. 2) of the wearer. Accordingly, the exterior shape of each insert 102 will vary somewhat so that it fits comfortably in the nasal passageways of the user. In the preferred embodiment the outer surfaces 108 will be tailored to the individual. However, it should be understood that the invention also includes making "pre-made" devices that are not tailored to particular individuals. The inserts 102 each have an interior passageway 106 through which air may travel and an outer surface 108 adapted to conform to the shape of the nasal passage of the individual wearer. The inserts 102 are formed from any flowable inert elastomeric material, such as vinyl poly siloxane or the like, that will become rigid enough to withstand collapse from the action of breathing through the nasal passages yet remain flexible enough to be inserted, worn, and removed without injuring or irritating the mucosa of the nasal passages. The material used for the inserts 102 may be any material, now known or later developed, which has relevant properties similar to the above mentioned materials. The inserts 102 are joined at the trailing, outer portion 110, and inserted at the leading, inner portion 112. The inserts 102 are generally tapered towards the leading portion 112. The amount of taper of the inserts 102 depends on the shape of the individual nasal passage to which the insert 102 conforms.

The first step in the formation of a nasal device 100 is to take a cast of the nasal passages of the wearer. The nasal passages are filled with a casting material, such as wax, and a negative cast of the nasal passages is produced inward about 0.75 inches for the average person. However, depth may be varied as necessary. The negative cast is used to produce a positive cast of the nasal passages. The positive cast is preferably made of a more permanent castable material, such as plaster. The positive cast is then filled with a flowable elastomeric material, such as vinyl poly siloxane. It is understood that the casting material may be any material now known or later developed for the purpose of making casts of body parts. In particular, any material suitable for dentures is also included. Due to this double casting process, the resulting nasal device 100 may, if desired, be slightly larger than the as-cast nasal passages. This may be desirable since the device may be used to expand or dilate collapsing nasal passages. It is also possible to size the device so that it merely prevents collapse of the nasal passageways.

Hollow passages are maintained in the dilator 100 while the flowable material cures. This can be achieved by slip-casting the nasal device 100 or providing rods completely through the nasal device 100 during curing. A connecting strip 104 is provided to join the separate inserts 102 of the nasal device 100. The connecting strip 104 serves to keep the pair of inserts 102 together as a unit, prevent over insertion into the nasal passages, and functions as a handle for removal of the nasal device 100 from the nose.

The above method of making the nasal device 100 is but one possible method. The nasal device 100 could alternatively be formed in the nasal cavity by placing the casting material therein and letting it harden. The openings 106 could be formed with an insert during casting or later drilled out.

Figure 2:
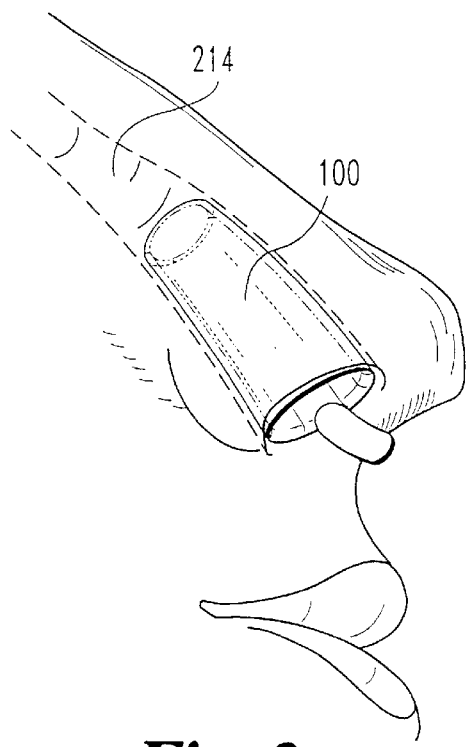
FIG. 2 is a side partial cross-sectional view of the preferred embodiment of the present invention as installed in a nasal passage.

FIG. 2 illustrates a nasal device 100 as installed in a nasal passage 214. The nasal device 100 conforms to the nasal passage 214 and fits snugly within, preventing collapse of the nasal passage 214. Alternatively, the nasal device 100 could be sized to slightly expand the nasal passageway 214. The nasal device 100 conforms to the natural shape of the individual wearer's nasal passages 214, to insure a comfortable fit and minimize irritation of the mucosa. The nasal device 100 may be worn at night during sleep, while eating, or at any other time to keep the nasal passages dilated to facilitate easy breathing.

It should be noted that the device may be made with any color desired including flesh tone.

Figure 3:
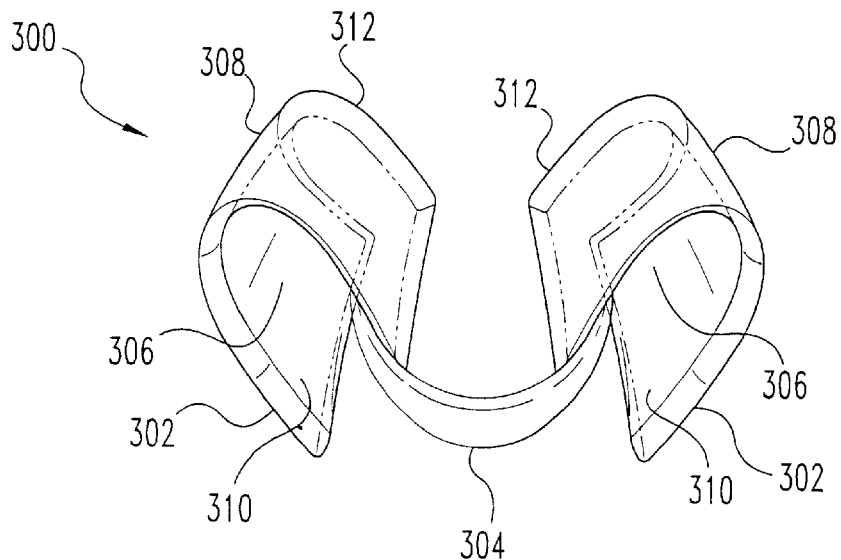
FIG. 3 is an isometric view of a second preferred embodiment of the present invention wherein the interior passageway is not completely surrounded as in the previous figures.

FIG. 3 shows a second preferred embodiment nasal device 300 having a pair of nasal inserts 302 joined by a connecting strip 304. The inserts 302 are arch-shaped, and define an interior breathing passageway 306 that is not completely enclosed. The outer surface 308 of each insert 302 is at least partially molded to the shape of the nasal passage (see FIG. 2) of the wearer. Accordingly, the exterior shape of each insert 302 will vary somewhat so that it fits comfortably in the nasal passageways of the user. In this embodiment the outer surfaces 308 will be tailored to the individual. The inserts 302 are formed from any flowable inert elastomeric material, such as vinyl poly siloxane or the like, that will become rigid enough to withstand collapse from the action of breathing through the nasal passages yet remain flexible enough to be inserted, worn, and removed without injuring or irritating the mucosa of the nasal passages. The material used for the inserts 302 may be any material, now known or later developed, which has relevant properties similar to the above mentioned materials. The inserts 302 are joined at the trailing, outer portion 310, and inserted at the leading, inner portion 312. The inserts 302 are generally tapered towards the leading portion 312. The open nature of the inserts 302 gives them additional flexibility to conform to the taper of the individual nasal passages.

The embodiment shown in FIG. 3 is one example of a nasal device 300 with partially open breathing passageways 306. It should be noted that other contemplated embodiments with openings located elsewhere, such as on the top or sides of the inserts 302, are also within the scope of the invention.

Figure 4:
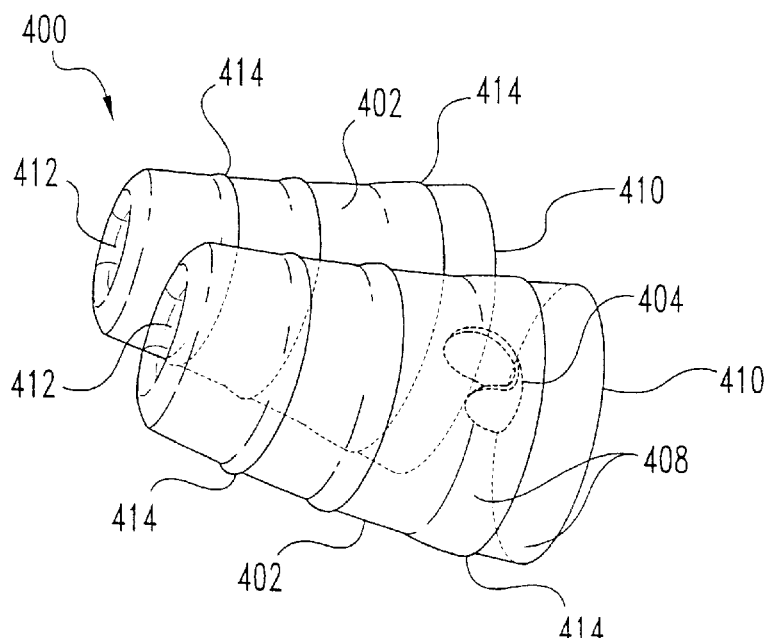
FIG. 4 is an isometric view of a third preferred embodiment of the present invention wherein the exterior surface is ridged.

FIG. 4 illustrates a third preferred embodiment nasal device 400 having a pair of nasal inserts 402 joined by a connecting strip 404. The inserts 402 have an interior breathing passageway 406 that is completely enclosed. The outer surface 408 of each insert 402 is molded to the general shape of the nasal passage (see FIG. 2) of the wearer. The outer surface is ribbed or ridged 414 in order to snugly and securely engage the nasal passages of the wearer. The inserts 402 are formed from any flowable inert elastomeric material, such as vinyl poly siloxane or the like, that will become rigid enough to withstand collapse from the action of breathing through the nasal passages yet remain flexible enough to be inserted, worn, and removed without injuring or irritating the mucosa of the nasal passages. The material used for the inserts 402 may be any material, now known or later developed, which has relevant properties similar to the above mentioned materials. The inserts 402 are joined at the trailing, outer portion 410, and inserted at the leading, inner portion 412. The inserts 402 are generally tapered towards the leading portion 412.

FIG. 4 illustrates one example of a ribbed or ridged 414 embodiment of the present invention. It should be noted that other ribbing or ridging configurations, such as larger or smaller or more or less frequent ridges are within the scope of the invention.

What is claimed is:

1. An insert to be placed in nasal passages comprising a pair of connected elastomeric members wherein the exterior surface of each member is molded to conform to a nasal passage so that said exterior surface substantially abuts the interior surface of said nasal passage, wherein the elastomeric members are connected by a connecting strip, and only the connecting strip remains outside of the nasal passages.

2. The insert of claim 1 wherein the elastomeric members are formed from vinyl poly siloxane.

3. The insert of claim 1 wherein the elastomeric members are flesh toned.

4. The insert of claim 1 wherein the elastomeric members are connected by a connecting strip.

5. The insert of claim 1 wherein the elastomeric members are ribbed.

6. A snore reduction device comprising a pair of hollow elastomeric inserts adapted to fit the nasal passages of the wearer so that the exterior surface of each of said inserts substantially abuts the interior surface of the respective nasal passage and the elastomeric inserts are connected by a connecting strip.

7. The device of claim 6 wherein the elastomeric inserts are formed from vinyl poly siloxane.

8. The device of claim 6 wherein the elastomeric inserts are flesh toned.

9. The insert of claim 6 wherein the elastomeric members are connected by a connecting strip.

10. A snore reduction device comprising twin elastomeric inserts adapted to fit the shape of the nasal cavities of the snorer, wherein each insert partially surrounds a breathing passage, wherein the elastomeric inserts are connected by a connecting strip.

11. The device of claim 10 wherein the elastomeric inserts are formed from vinyl poly siloxane.

12. The device of claim 10 wherein the elastomeric inserts are flesh toned.

13. The insert of claim 10 wherein the elastomeric members are connected by a connecting strip.

14. A method of producing a snore reduction device comprising the steps of:

providing a person having a pair of nasal passages respectively terminated by a pair of nostrils;

making a negative cast of the interior surfaces of the nasal passages of the person from the nostrils inward;

making a positive cast of the nasal passages from the negative cast;

filling the positive cast of the nasal passages with a flowable elastomeric material;

inserting a solid rod completely through each of the elastomeric forms;

allowing the elastomeric forms to cure;

removing the rods from the solidified elastomeric forms;

connecting the elastomeric forms with an elastomeric joiner.

15. A nasal device comprising:

a first nasal insert member comprising an exterior surface and an interior surface defining a breathing passageway, the exterior surface substantially conforming to at least a portion of a first nasal passageway;

a second nasal insert member comprising an exterior surface and an interior surface defining a breathing passageway, the exterior surface substantially conforming to at least a portion of a first nasal passageway;

a connecting member joined to the first and second nasal insert members; and said connecting member being the only part of the device that remains outside of said nasal passageways.

16. The nasal device of claim 15 wherein the first and second nasal inserts contain an elastomeric material.

17. The nasal device of claim 16 wherein the elastomeric material comprises vinyl poly siloxane.

18. The nasal device of claim 15 wherein the first and second nasal inserts contain denture material.

19. The nasal device of claim 15 wherein the exterior surfaces of the first and second nasal inserts are ribbed.

* * * * *